United States Patent [19]

Elbe

[11] Patent Number: 4,625,066
[45] Date of Patent: Nov. 25, 1986

[54] SUBSTITUTED ACETYLENE-KETONES

[75] Inventor: Hans-Ludwig Elbe, Wuppertal, Fed. Rep. of Germany

[73] Assignee: Bayer Aktiengesellschaft, Leverkusen, Fed. Rep. of Germany

[21] Appl. No.: 676,128

[22] Filed: Nov. 29, 1984

[30] Foreign Application Priority Data

Dec. 1, 1983 [DE] Fed. Rep. of Germany ....... 3343531

[51] Int. Cl.[4] .......................................... C07C 49/217
[52] U.S. Cl. .................................... 568/308; 568/31;
568/29; 568/37; 568/42; 568/43; 568/376;
568/375; 568/377; 568/379; 568/380; 568/381;
568/329; 568/330; 568/305; 568/306; 568/307;
568/417; 568/415; 568/418; 560/51
[58] Field of Search ............... 568/417, 418, 307, 329,
568/322, 323, 308, 31, 29, 37, 42, 43, 376, 375,
377, 379, 380, 381, 329, 330, 305, 306, 307, 417,
415; 560/51; 260/465 D

[56] References Cited

U.S. PATENT DOCUMENTS

| | | | |
|---|---|---|---|
| 2,937,205 | 5/1960 | Robertson | 568/308 |
| 3,409,424 | 11/1968 | Brewbaker et al. | 568/323 |
| 3,513,202 | 5/1970 | Chretien et al. | 568/417 |
| 3,839,455 | 10/1974 | Scherm et al. | 568/322 |
| 4,382,944 | 5/1983 | Krämer et al. | 568/308 |
| 4,385,185 | 5/1983 | Gebauer et al. | 568/308 |

FOREIGN PATENT DOCUMENTS

| | | | |
|---|---|---|---|
| 703522 | 12/1979 | U.S.S.R. | 568/322 |
| 570257 | 6/1980 | U.S.S.R. | 568/322 |

OTHER PUBLICATIONS

Agr. Biol. Chem. 39, 519–527 (1975).
Helv. Chim. Acta, 62, 852–865 (1979).

Primary Examiner—James H. Reamer
Attorney, Agent, or Firm—Sprung, Horn, Kramer & Woods

[57] ABSTRACT

Novel substituted acetylene-ketones of the formula $$R^2-C\equiv C-CO-R^1 \quad (I)$$

in which
$R^1$ represents optionally substituted cycloalkyl with 4 to 7 carbon atoms or the groupings

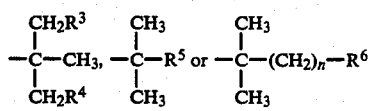

or represents optionally substituted aryl, if $R^2$ represents optionally substituted cycloalkenyl or optionally substituted cycloalkylalkyl;
$R^2$ represents alkyl, optionally substituted cycloalkyl, optionally substituted cycloalkenyl, optionally substituted cycloalkylalkyl, optionally substituted aryl or optionally substituted aralkyl;
$R^3$ represents halogen;
$R^4$ represents hydrogen or halogen;
$R^5$ represents alkyl with more than 1 carbon atom, alkenyl, alkinyl or the CHO group or a derivative thereof, or represents methyl, if $R^2$ represents optionally substituted cycloalkenyl or optionally substituted cycloalkylalkyl;
$R^6$ represents cyano, optionally substituted aryl or the groupings $-XR^7$ or $-CONR^8R^9$;
$R^7$ represents alkyl, halogenoalkyl, optionally substituted aryl or optionally substituted aralkyl;
$R^8$ represents hydrogen, alkyl or optionally substituted aryl;
$R^9$ represents hydrogen or alkyl;
X represents O, S, SO or $SO_2$ and
the index n represents the numbers 0 or 1.

The new compounds are valuable intermediates for the synthesis of substances having plant growth-regulating and fungicidal properties.

8 Claims, No Drawings

SUBSTITUTED ACETYLENE-KETONES

The present invention relates to new substituted acetylene-ketones. The new compounds are valuable intermediates for the synthesis of substances having plant growth-regulating and fungicidal properties.

It has already been disclosed that azolyl-methyl-ketones can be used as intermediates for the preparation of azolyl derivatives having plant growth-regulating and fungicidal properties (compare European Patent Specification 0,032,200 and European Patent Specification 0,031,911). Thus, for example, 1-cyclohexyl-2-(1,2,4-triazol-1-yl)-4,4-bis-fluoromethyl-pentan-3-one can be synthesised by reacting 1-(1,2,4-triazol-1-yl)-3,3-bis-fluoromethyl-butan-2-one with cyclohexyl-methyl bromide according to the following equation:

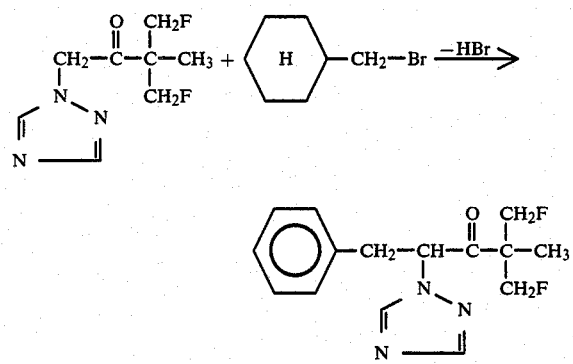

However, the disadvantage is that in this type of preparation of azolyl derivatives having a plant growth-regulating and fungicidal activity, the azolyl-methyl-ketones required as intermediates are obtainable only by multi-stage syntheses and some of the materials thereby used as starting substances are accessible only with difficulty.

The present invention now provides, as new compounds, the substituted acetylene-ketones of the formula

  (I)

in which
$R^1$ represents optionally substituted cycloalkyl with 4 to 7 carbon atoms or the groupings

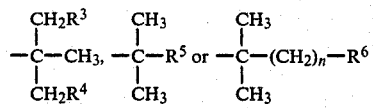

or represents optionally substituted aryl, if $R^2$ represents optionally substituted cycloalkenyl or optionally substituted cycloalkylalkyl;
$R^2$ represents alkyl, optionally substituted cycloalkyl, optionally substituted cycloalkenyl, optionally substituted cycloalkylalkyl, optionally substituted aryl or optionally substituted aralkyl;
$R^3$ represents halogen;
$R^4$ represents hydrogen or halogen;
$R^5$ represents alkyl with more than 1 carbon atom, alkenyl, alkinyl or the CHO group or a derivative thereof, or represents methyl, if $R^2$ represents optionally substituted cycloalkenyl or optionally substituted cycloalkylalkyl;
$R^6$ represents cyano, optionally substituted aryl or the groupings $-XR^7$ or $-CONR^8R^9$;
$R^7$ represents alkyl, halogenoalkyl, optionally substituted aryl or optionally substituted aralkyl;
$R^8$ represents hydrogen, alkyl or optionally substituted aryl;
$R^9$ represents hydrogen or alkyl;
X represents O, S, SO or $SO_2$ and
the index n represents the numbers 0 or 1.

The new substituted acetylene-ketones of the formula (I) are obtained by a process, which comprises reacting an acetylene derivative of the formula

  (II)

in which
$R^2$ has the abovementioned meanings and
M represents a metal or hydrogen;
with an acid derivative of the formula

  (III)

in which
$R^1$ has the abovementioned meanings and
Y represents an electron-withdrawing leaving grouping,
if appropriate in the presence of a diluent, and, in addition, if appropriate in the presence of a base and of Cu-(I) ions as a catalyst.

It has also been found that the new substituted acetylene-ketones of the formula (I) are particularly suitable as intermediates for the preparation of azolyl derivatives having a plant growth-regulating and fungicidal activity.

Surprisingly, azolyl-ketones and -carbinols having a plant growth-regulating and fungicidal action can be prepared from the substituted acetylene-ketones of the formula (I) according to the invention more simply and in a higher yield than by the processes known hitherto, in which the corresponding azolylmethyl-ketones have been used as intermediates.

Formula (I) provides a general definition of the new substituted acetylene-ketones. Preferably, in this formula (I)
$R^1$ represents cycloalkyl which has 4 to 7 carbon atoms and is optionally mono-, di- or tri-substituted by identical or different alkyl radicals with 1 to 4 carbon atoms, or the groupings

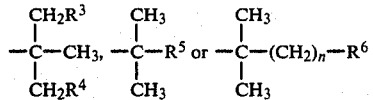

or represents phenyl which is optionally mono-, di- or tri-substituted by identical or different substituents if $R^2$ represents optionally substituted cycloalkenyl or optionally substituted cycloalkyl, possible substituents being the substituents on phenyl mentioned for $R^2$;
$R^2$ represents straight-chain or branched alkyl with 1 to 12 carbon atoms, or represents cycloalkyl or cycloalkylalkyl with in each case 3 to 7 carbon atoms in the cycloalkyl part and 1 to 4 carbon atoms in the alkyl part and in each case optionally mono-, di- or tri-substituted by identical or different alkyl radicals with 1 to 4 carbon atoms, or represents cycloalkenyl with 5 to 7 carbon atoms optionally mono-, di- or tri-substituted by identical or different alkyl radicals with 1 to 4 carbon atoms, or represents phenyl or phenylalkyl with 1 to 4 carbon atoms in the alkyl part, each of which is optionally mono-, di- or tri-substituted by identical or different substituents, substituents on the phenyl which may be mentioned in each case being: halogen; alkyl, alkoxy and alkylthio with in each case 1 to 4 carbon atoms; halogenoalkyl, halogenoalkoxy and halogenoalkylthio with in each case 1 to 4 carbon atoms and 1 to 5 identical or different halogen atoms, such as fluorine and chlorine atoms; nitro, cyano, alkoxycarbonyl with 1 to 4 carbon atoms in the alkoxy part, and in each case optionally halogeno-substituted phenyl and phenoxy;

$R^3$ represents fluorine, chlorine or bromine;

$R^4$ represents hydrogen, fluorine, chlorine or bromine;

$R^5$ represents straight-chain or branched alkyl with 2 to 6 carbon atoms, straight-chain or branched alkenyl with 2 to 4 carbon atoms, straight-chain or branched alkinyl with 3 to 5 carbon atoms, or the —CH═O group or a derivative thereof, such as an oxime, oxime ether or acetal, for example alkoximinomethyl with 1 to 4 carbon atoms in the alkoxy part, dialkoxymethyl with 1 to 4 carbon atoms in each alkoxy part or optionally substituted dioxolane or dioxane; or furthermore represents methyl, if $R^2$ represents optionally substituted cycloalkenyl or optionally substituted cycloalkylalkyl;

$R^6$ represents cyano, or represents phenyl which is optionally mono-, di- or tri-substituted by identical or different substituents, possible substituents being the substituents on phenyl which have already been mentioned for $R^2$, or represents the groupings —$XR^7$ or —$CONR^8R^9$;

$R^7$ represents straight-chain or branched alkyl with 1 to 6 carbon atoms, halogenoalkyl with 1 to 4 carbon atoms and 1 to 5 identical or different halogen atoms, such as fluorine and chlorine atoms, or represents phenyl or phenylalkyl with 1 or 2 carbon atoms in the alkyl part, in each case optionally mono-, di- or tri-substituted by identical or different substituents, possible substituents in each case being the substituents on phenyl which have already been mentioned for $R^2$;

$R^8$ represents hydrogen, straight-chain or branched alkyl with 1 to 4 carbon atoms or phenyl which is optionally mono-, di- or tri-substituted by identical or different substituents, possible substituents being substituents on phenyl which have already been mentioned for $R^2$;

$R^9$ represents hydrogen or straight-chain or branched alkyl with 1 to 4 carbon atoms; and X and the index n have the meanings given in the definition of the invention.

Particularly preferred compounds of the formula (I) are those in which $R^1$ represents cyclobutyl, cyclopentyl or cyclohexyl, optionally mono- or di-substituted by identical or different substituents from the group comprising methyl, ethyl, isopropyl and tert.-butyl, or represents the groupings

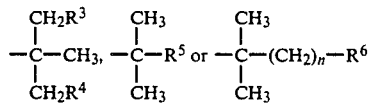

or represents phenyl which is optionally mono- or di-substituted by identical or different substituents if $R^2$ represents optionally substituted cycloalkenyl or optionally substituted cycloalkylalkyl, possible substituents being the substituents on phenyl mentioned for $R^2$;

$R^2$ represents straight-chain or branched alkyl with 1 to 6 carbon atoms, or represents cyclopropyl, cyclopropylmethyl, cyclopentyl, cyclopentylmethyl, cyclohexyl, cyclohexylmethyl, cycloheptyl, cyclopentenyl, cyclohexenyl or cycloheptenyl, each of which is optionally mono- or di-substituted by identical or different substituents from the group comprising methyl, ethyl, isopropyl and/or tert.-butyl, or represents phenyl or phenylalkyl with 1 or 2 carbon atoms in the alkyl part, in each case optionally mono- or di-substituted by identical or different substituents, substituents on the phenyl which may be mentioned in each case being: fluorine, chlorine, methyl, ethyl, isopropyl, tert.-butyl, methoxy, methylthio, trifluoromethyl, trifluoromethoxy, trifluoromethylthio, nitro, cyano, methoxycarbonyl and phenyl and phenoxy, in each case optionally substituted by chlorine or fluorine;

$R^3$ represents fluorine or chlorine;

$R^4$ represents hydrogen, fluorine or chlorine;

$R^5$ represents straight-chain or branched alkyl with 2 to 6 carbon atoms, vinyl, propargyl, the —CH═O— group, methoximinomethyl, dimethoxymethyl or the dioxolane or 1,3-dioxane radical;

$R^6$ represents cyano, or phenyl which is optionally mono- or di-substituted by identical or different substituents, possible substituents being the substituents on phenyl which have already been mentioned for $R^2$, or represents the groupings —$XR^7$ or —$CONR^8R^9$;

$R^7$ represents straight-chain or branched alkyl with 1 to 4 carbon atoms, halogenoalkyl with 1 or 2 carbon atoms and 1 to 5 identical or different halogen atoms, such as fluorine and chlorine atoms, or represents phenyl or benzyl, in each case optionally mono- or poly-substituted by identical or different substituents, possible substituents in each case being the substituents on phenyl which have already been mentioned for $R^2$;

$R^8$ represents hydrogen, methyl, ethyl or isopropyl, or represents phenyl which is optionally mono- or di-substituted by identical or different substituents, possible substituents being the substituents on phenyl which have already been mentioned for $R^2$;

$R^9$ represents hydrogen, methyl or isopropyl; and

X and the index n have the meanings given in the definition of the invention.

Especially preferred compounds of the formula (I) are those in which $R^1$ represents the grouping

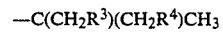

wherein $R^3$ represents fluorine or chlorine and $R^4$ represents hydrogen, fluorine or chlorine.

If, for example, α-fluoromethyl-α-methylpropionyl chlorine and the lithium salt of phenylacetylene are used as starting substances, the course of the reaction in the process according to the invention can be represented by the following equation:

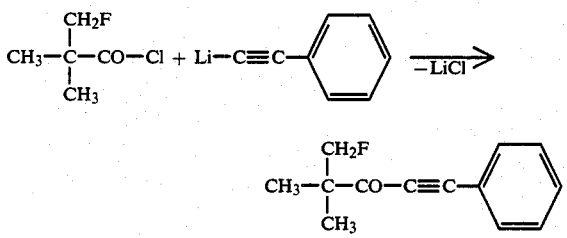

If, for example, α,α-bisfluoromethylpropionyl chloride and phenylacetylene are used as starting substances, copper-(I) bromide is used as the catalyst and triethylamine is used as the base, the course of the reaction in the process according to the invention can be represented by the following equation:

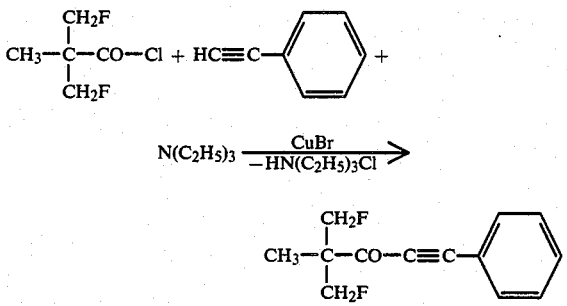

Formula (II) provides a general definition of the acetylene derivatives to be used as starting substances for carrying out the process according to the invention. In this formula, $R^2$ preferably has those meanings which have already been mentioned as preferred for this substituent in connection with the description of the substances of the formula (I) according to the invention. M preferably represents hydrogen or a corresponding equivalent of an alkali metal or alkaline earth metal, such as, for example, lithium, sodium or magnesium.

The acetylene derivatives of the formula (II) are generally known compounds of organic chemistry, or they can be obtained in a generally known manner (in this context compare, for example, Tetrahedron 37 (1981), 1653–1658; J. Chem. Research 1978, 106–107; 1979, 130 and 1981, 270–271; and Houben-Weyl, Methoden der organischen Chemie (Methods of Organic Chemistry), volume V/2a, page 351 et seq.).

Formula (III) provides a general definition of the acid derivatives also to be used as starting substances for the process according to the invention. In this formula, $R^1$ preferably has the meanings which have already been mentioned as preferred for this substituent in connection with the description of the substances of the formula (I) according to the invention. Y represents an electron-withdrawing leaving group, such as, preferably, halogen, p-methylphenylsulphonyloxy or the groupings —O—SO₂—OR or —NR₃, R representing an optionally substituted hydrocarbon radical.

The acid derivatives of the formula (III) are generally known compounds of organic chemistry, or they can be obtained in a generally known manner (in this context, compare, for example, U.S. Pat. No. 3,414,612, DE-OS (German Published Specification) 3,128,445 and EP-OS (European Published Specification) 0,049,416).

Possible diluents for the process according to the invention are inert organic solvents. These include, preferably, aromatic hydrocarbons, such as toluene, xylene or chlorobenzene; nitriles, such as acetonitrile; ethers, such as diisobutyl ether or dioxane; and pyridine.

The reaction temperatures can be varied within a substantial range in carrying out the process according to the invention. In general, the reaction is carried out in the range between 0° C. and 150° C., preferably between 20° C. and 120° C.

Preferred possible bases for the process according to the invention are tertiary amines. Bases which may be mentioned in particular here are: triethylamine, N,N-dimethylcyclohexylamine and N,N-dimethylbenzylamine.

Copper-(I) chloride and copper-(I) bromide are preferred possible catalytically active substances for carrying out the process according to the invention.

In carrying out the process according to the invention, the compounds of the formulae (II) and (II) are preferably reacted in equimolar amounts. In many cases, it is advisable to add a base as an acid-binding agent and a copper-(I) salt as a substance acting as a catalyst. The compounds of the formula (I) are worked up and isolated by customary methods.

As already mentioned, the new substituted acetylene-ketones of the formula (I) are interesting intermediates for the synthesis of active compounds having fungicidal and plant growth-regulating properties. Thus, azolyl-ketones and -carbinols of the formula (IV)

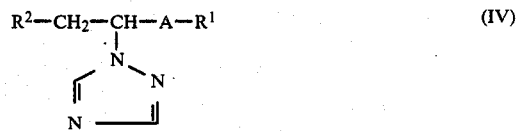

in which
$R^1$ and $R^2$ have the abovementioned meanings and
A represents the keto group or the CH(OH) group, are obtained by reacting substituted acetylene-ketones of the formula (I)

in which $R^1$ and $R^2$ have the abovementioned meanings, selectively (without attack of the CO group) with hydrogen in the presence of a hydrogenation catalyst and, preferably, in the presence of a diluent; subsequently reacting the ketones thus obtained, of the formula (V)

in which $R^1$ and $R^2$ have the abovementioned meanings, with chlorine or bromine in the presence of an inert organic solvent, such as, for example, ether or chlorinated or non-chlorinated hydrocarbons, at room temperature, or with customary chlorinating agents, such as, for example, sulphuryl chloride, at 20° C. to 60° C.; thereafter reacting the halogenoketones thus obtain, of the formula (VI)

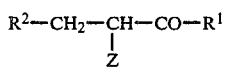

$$R^2\text{—}CH_2\text{—}CH\text{—}CO\text{—}R^1 \quad (VI)$$
$$|$$
$$Z$$

in which $R^1$ and $R^2$ have the abovementioned meanings and Z represents chlorine or bromine,
with 1,2,4-triazole in the presence of an inert organic solvent, such as, for example, acetonitrile, and in the presence of an acid-binding agent, such as, for example, potassium carbonate, or in the presence of an excess of 1,2,4-triazole, at temperatures between 60° C. and 120° C.; and, if appropriate, subsequently reducing the azolylketones thus obtained, of the formula (IVa)

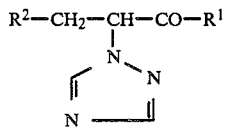

in which $R^1$ and $R^2$ have the abovementioned meanings, by reaction with complex hydrides, such as sodium borohydride or lithium alanate, in the presence of a polar organic solvent, such as, for example, an alcohol, at temperatures between 0° C. and 30° C.; or reducing the products by reaction with aluminium isopropylate in the presence of a diluent, such as, for example, isopropanol, at temperatures between 20° C. and 120° C.

The hydrogenation reactions in the first stage of the process described above are carried out in the liquid phase, preferably in the presence of diluents, using a suspended, pulverulent hydrogenation catalyst. Dehydrogenation reactions can be carried out discontinuously (batchwise) or continuously as a liquid phase or trickle phase hydrogenation reaction in known hydrogenation reactors, such as autoclaves, autoclave cascades, tube reactors or circulatory reactors. The preferred procedure is discontinuous liquid phase hydrogenation in an autoclave under increased pressure.

Possible diluents for the hydrogenation reactions are inert organic solvents. These include, preferably, alcohols, such as methanol, ethanol, isopropanol or ethylene glycol; ethers, such as diethyl ether, diisopropyl ether, ethylene glycol monomethyl ether, ethylene glycol dimethyl ethers, dioxane or tetrahydrofuran; saturated hydrocarbons, such as n-heptane or cyclohexane; and esters, such as ethyl acetate.

Examples of hydrogenation catalysts which are suitable for the hydrogenation reactions are those which consist of, or contain, metals and/or compounds of elements of sub-group eight of the Mendeleev periodic table of the elements. The metals ruthenium, rhodium, palladium, platinum, cobalt and nickel and compounds thereof are preferred here. The metal compounds can be, for example, oxides, hydroxides and/or hydrated oxides. In addition, the metals copper, vanadium, molybdenum, chromium and/or manganese, and compounds of these metals, can be present.

The hydrogenation catalysts can consist exclusively or predominantly of substances which transfer hydrogen; however, these can also be applied to supports.

Examples of possible supports for the substances which transfer hydrogen are: inorganic materials, such as kieselguhr, silicic acid, aluminium oxides, alkali metal and alkaline earth metal silicates, aluminium silicates, montmorillonite, zeolites, spinels, dolomite, kaolin, magnesium silicates, zirconium oxide, zinc oxide, calcium carbonate, silicon carbide, aluminium phosphate, boron phosphate, asbestos, active charcoal or barium sulphate, and also organic materials, for example naturally occuring or synthetic compounds with high molecular weights, such as silk, polyamides, polystyrenes, cellulose or polyurethanes. Inorganic supports in powder form are preferred.

Such supported catalysts can in general contain 0.5 to 50% by weight, preferably 1 to 10% by weight, of the substances which transfer hydrogen, based on the total weight of the supported catalyst. The substance which transfers hydrogen can thereby be homogeneously distributed in the support, but catalysts containing a deposit of the substance which transfers hydrogen in their outer layer or on their surface are preferred. Catalysts which can be used in the process according to the invention can be prepared and shaped in a known manner (compare, for example, Houben-Weyl, Methoden der organischen Chemie (Methods of Organic Chemistry), volume IV, 1c, part I, pages 16–26, Georg Thieme Verlag, Stuttgart, 1980).

Preferred catalysts are ruthenium-on-charcoal, ruthenium-on-aluminium oxide, rhodium-on-charcoal, rhodium-on-aluminium oxide, palladium-on-calcium carbonate, palladium-on-barium sulphate, palladium-on-silicic acid, platinum-on-charcoal and platinum-on-aluminium oxide, nickel-on-kieselguhr, nickel-on-aluminium oxide and nickel and palladium-on-aluminium oxide.

Examples of preferred hydrogenation catalysts which consist exclusively or predominantly of the substance which transfers hydrogen are oxidic catalysts, such as palladium oxide, platinum oxide, ruthenium oxide and/or rhodium oxide/platinum oxide according to Nishimura, and furthermore black catalysts which can be prepared by reduction of corresponding metal salts or metal salt mixtures with alkali metal hydrides, alkali metal carbonates, metal-alkyls, hydrazine, formaldehyde, hydrogen or more electropositive metals, such as palladium black, platinum black and rhodium black; as well as skeleton catalysts of the Raney type, such as Raney nickel cobalt, Raney nickel/cobalt, Raney nickel/iron, Raney nickel/copper, Raney nickel/iron/chromium, Raney nickel/palladium and Raney nickel/iron/vanadium.

The selection of one or more of the hydrogenation catalysts mentioned advantageously depends on the structure of the acetylene-ketones of the formula (I) to be hydrogenated and/or the desired active compounds of the formula (IV).

The hydrogenation catalysts are used in an amount such that 0.05 to 2.5, preferably 0.1 to 1% by weight of the substance which transfers hydrogen is present, based on the total weight of the reaction mixture.

Mixtures of two or more of the hydrogenation catalysts mentioned can also be used in carrying out the hydrogenation.

The reaction temperatures can be varied within a substantial range in the hydrogenation. In general, the reaction is carried out in the range between 0° C. and 150° C., preferably between 20° C. and 120° C.

The hydrogenation is preferably carried out under increased pressure. In general, it is carried out between 1 and 150 bar, preferably under 20 to 120 bar.

The azolyl-ketones and -carbinols of the formula (IV) have powerful fungicidal and plant growth-regulating properties (compare EP-OS (European Published Specification) 0,031,911, EP-OS (European Published Specification) 0,032,200, EP-OS (European Published Specification) 0,055,833 and EP-OS (European Published Specification) 0,054,865 and DE-OS (German Published Specification) 3,224,129).

The preparation and use of the substances according to the invention can be seen from the following examples.

PREPARATION EXAMPLES

Example 1

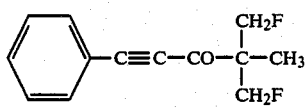

10.1 g (0.1 mole) of triethylamine and 1.43 g (0.01 mole) of copper-(I) bromide were initially introduced into 30 ml of pyridine under nitrogen. 10.2 g (0.1 mole) of phenylacetylene were added and the mixture was subsequently stirred for 30 minutes. Thereafter, 15.6 g (0.1 mole) of α,α-bisfluoromethyl-propionyl chloride were added dropwise to the reaction mixture and the temperature was thereby kept at 60° C. The mixture was stirred at this temperature for 15 hours and then cooled, washed with water, dried over sodium sulphate and concentrated in vacuo. The residue was purified by distillation.

17.3 g (78% of theory) of 2,2-bisfluoromethyl-5-phenyl-4-pentin-3-one of boiling point 103° C. to 105° C./0.2 mbar were obtained.

Example 2

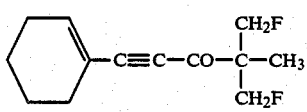

10.1 g (0.1 mole) of triethylamine and 1.43 g (0.01 mole) of copper-(I) bromide were initially introduced into 30 ml of pyridine under nitrogen. 10.6 g (0.1 mole) of cyclohexan-1-yl-acetylene were added and the mixture was subsequently stirred for 20 minutes. Thereafter, 15.6 g (0.1 mole) of α,α-bisfluoromethyl-propionyl chloride were added dropwise to the reaction mixture and the temperature was kept at 70° C. The mixture was stirred at this temperature for 15 hours and then cooled, washed with water, dried over sodium sulphate and concentrated in vacuo. The residue was purified by distillation.

18.1 g (80% of theory) of 2,2-bisfluoromethyl-5-cyclohexen-1-yl-4-pentin-3-one of boiling point 106° C. to 109° C./0.3 mbar were obtained.

The following acetylene-ketones of the formula (I) were obtained in an analogous manner and according to the process conditions described:

TABLE 1

| Example No. | $R^2-C\equiv C-COR^1$ $R^1$ | $R^2$ | (I) Melting point (°C.) or boiling point (°C.)/mbar or $n_D^{20}$ |
|---|---|---|---|
| 3 | (ClCH$_2$)$_2$(CH$_3$)C— | phenyl | 1.5465 |
| 4 | (ClCH$_2$)$_2$(CH$_3$)C— | cyclohexenyl | 44 |
| 5 | Cl—C$_6$H$_4$—O—CH$_2$—C(CH$_3$)$_2$ | cyclohexenyl | 60 |
| 6 | C$_2$H$_5$—C(CH$_3$)$_2$ | cyclohexenyl | 1.5202 |
| 7 | FCH$_2$—C(CH$_3$)$_2$ | cyclohexenyl | 99–103 |
| 8 | cyclobutyl-CH$_3$ | cyclohexenyl | 109–113 |
| 9 | Cl—C$_6$H$_4$— | cyclohexenyl | 84 |
| 10 | (FCH$_2$)$_2$(CH$_3$)C— | C$_4$H$_9$ | 70–73/0.1 |

PREPARATION OF (1,2,4-TRIAZOL-1-YL) DERIVATIVES OF THE FORMULA (IV)

Example 11

1st stage

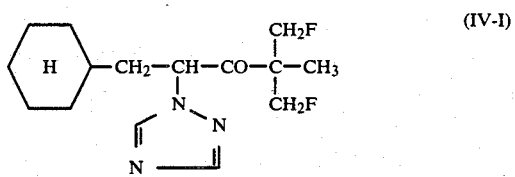
(IV-I)

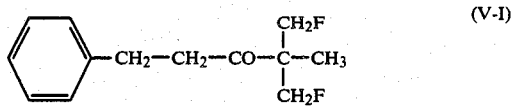
(V-I)

A 0.3 liter stainless steel stirred autoclave, which can be temperature-controlled with the aid of an adjustable thermostat, was charged with 4.4 g (0.2 mole) of 2,2-bisfluoromethyl-5-phenyl-4-petin-3-one (Example 1), 170 ml of methanol and 5 g of Raney nickel.

After the autoclave had been closed and the air had been displaced with nitrogen, the mixture employed was charged with hydrogen up to a pressure of 30 bar and heated at 30° C., with stirring. As soon as this temperature was reached, the hydrogen pressure was increased to 50 bar and was maintained at this level in accordance with the rate of consumption of the hydrogen throughout the entire reaction time.

When the uptake of hydrogen had ended, after about 2 hours, stirring was continued under the abovementioned hydrogenation conditions for a further hour in order to bring the reaction to completion, and the mixture was then cooled to room temperature and let down to normal pressure.

The product solution removed from the catalyst by filtration was freed from the methanol in a rotary evaporator.

44.5 g (98.5% of theory) of 2,2-bisfluoromethyl-5-phenyl-3-pentanone were obtained as an oil with a content of 96.5% (determined by gas chromatography).

2nd stage

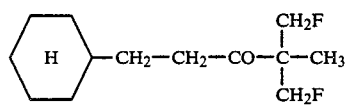
(V-2)

A 120 liter stainless steel stirred autoclave which can be temperature-controlled with the aid of an adjustable thermostat was charged with a solution of 29.7 kg (131.4 moles) of 2,2-bisfluoromethyl-5-phenyl-3-pentanone in 60 liters of methanol and 0.72 kg of a catalyst containing 5% of ruthenium on active charcoal.

After the autoclave had been closed and the air had been displaced with nitrogen, the mixture employed was charged with hydrogen up to a pressure of 50 bar and heated to 90° C., with stirring. As soon as this temperature was reached, the hydrogen pressure was increased to 100 bar and was maintained at this level in accordance with the rate of consumption of the hydrogen throughout the entire reaction time.

When the uptake of hydrogen had ended, after about 6 hours, stirring was continued under the abovementioned hydrogenation conditions for a further hour in order to bring the reaction to completion, and the mixture was then cooled to room temperature and let down to normal pressure.

The product solution removed from the catalyst by filtration was freed from the methanol in a rotary evaporator.

30.3 kg (99.4% of theory) of 2,2-bisfluoromethyl-5-cyclohexyl-3-pentanone were obtained as an oil with a content of 96% (determined by gas chromatography).

3rd stage

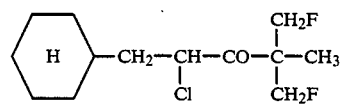
(VI-I)

232 g (1 mole) of 2,2-bisfluoromethyl-5-cyclohexyl-3-pentanone were heated to 80° C. and 161.9 g (1.2 moles) of sulphuryl chloride were added dropwise in the course of one hour. The mixture was subsequently stirred at 80° C. for 5 hours and excess sulphuryl chloride was then distilled off in vacuo. After the mixture had been cooled to 20° C., 500 ml of methyl isobutyl ketone were added. The organic solution was washed neutral with water, dried over magnesium sulphate and concentrated in vacuo. The residue was distilled.

252 g (90% of theory) of 2,2-bisfluoromethyl-4-chloro-5-cyclohexyl-3-pentanone of boiling point 118° C. to 120° C./2.5 mbar were obtained.

4th stage

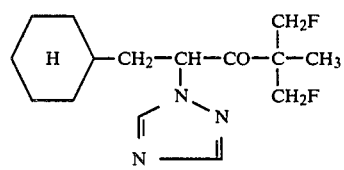
(IV-I)

A mixture of 266.7 g (1 mole) of 2,2-bisfluoro-4-chloro-5-cyclohexyl-3-pentanone, 69.1 g (1 mole) of 1,2,4-triazole and 165.8 g (1.2 moles) of potassium carbonate in 1000 ml of methyl isobutyl ketone was heated under reflux for 6 hours. After cooling, the mixture was washed with dilute hydrochloric acid and washed neutral with water. The organic phase was dried over magnesium sulphate and concentrated in vacuo. 329 g (88% of theory) of 2,2-bisfluoromethyl-5-cyclohexyl-4-(1,2,4-triazol-1-yl)-3-pentanone of refractive index $n_D^{20}$: 1.4933 were obtained.

Example 12

1st stage

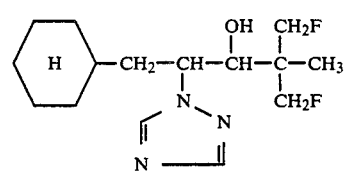
(IV-2)

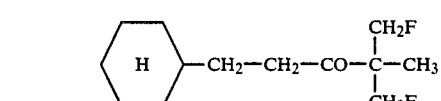
(V-I)

A 0.3 liter stainless steel stirred autoclave which can be temperature-controlled with the aid of an adjustable thermostat was charged with 24 g (0.106 mole) of 2,2-bisfluoromethyl-5-cyclohexen-1-yl-pentin-3-one (Example 2), 120 ml of methanol and 5 g of Raney nickel.

After the autoclave had been closed and the air had been displaced with nitrogen, the mixture employed was charged with hydrogen up to a pressure of 50 bar and heated to 50° C., with stirring. As soon as this temperature was reached, the hydrogen pressure was increased to 70 bar and was maintained at this level in accordance with the rate of consumption of the hydrogen throughout the entire reaction time.

When the uptake of hydrogen had ended, stirring was continued under the abovementioned hydrogenation conditions for a further hour and the mixture was then cooled to room temperature and let down to normal pressure.

The product solution separated off from the catalyst by filtration was freed from the methanol on a rotary evaporator.

23.5 g (95.5% of the theory) of 2,2-bisfluoro-methyl-5-cyclohexyl-3-pentanone were obtained as an oil with a content of 88.5% (determined by gas chromatography).

2nd stage

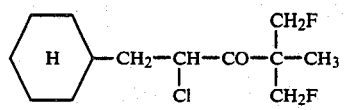 (VI-I)

The second stage was carried out in the same way as the third stage of Example 11.

3rd stage

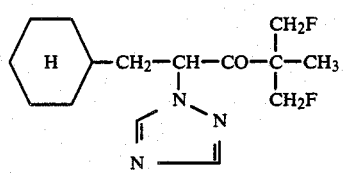 (IV-1)

The third stage was carried out in the same way as the 4th stage of Example 11.

4th stage

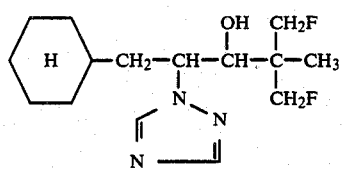 (IV-2)

299 g (1 mole) of 2,2-bisfluoromethyl-5-cyclohexyl-4-(1,2,4-triazol-1-yl)-3-pentanone were dissolved in 300 ml of methanol and a solution of 13.2 g (0.35 mole) of sodium borohydride in 150 ml of 0.1 normal aqueous sodium hydroxide solution was added dropwise at 0° C. to 5° C. After a reaction time of 2 hours, the reaction solution was brought to a pH value of 4 to 5 with dilute hydrochloric acid. After addition of 500 ml of water, the end product crystallised out.

After drying in vacuo, 286 g (95% of theory) of 2,2-bisfluoromethyl-5-cyclohexyl-4-(1,2,4-triazol-1-yl)-3-pentanol of melting point 103° C. to 105° C. were obtained.

COMPARISON EXAMPLE

Preparation of the 1,2,4-triazol-1-yl derivative of the formula

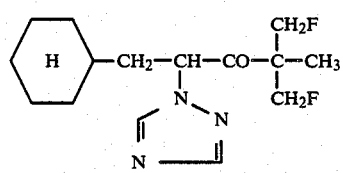

by the process known hitherto.

1st stage

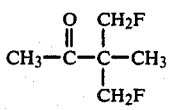

400 ml of tetraethylene glycol and 46.4 g of potassium fluoride (0.8 mole) were initially introduced into a three-necked flask with a stirrer, dropping funnel and Liebig condenser with a cooled receiver, and were heated to 170° C. A waterpump vacuum (pressure about 20 to 30 mbar) was applied to the adaptor of the Liebig condenser. 57.6 g (0.2 mole) of 2-acetyl-2-methylpropane-1,3-diol bismethanesulphate, dissolved in 100 ml of tetraethylene glycol, were then added dropwise in the course of 45 minutes. The 3,3-bisfluoromethyl-butan-2-one formed was distilled off into the cooled receiver during the reaction. After the dropwise addition, distillation was continued at 175° C. for a further hour. The distillate collected was then redistilled. 14 g (51.5% of theory) of 3,3-bisfluoromethylbutan-2-one of boiling point 43° to 46° C./12 mbar were obtained.

2nd stage

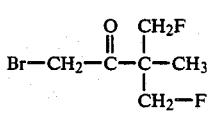

51 ml (1 mole) of bromine were added dropwise to 136 g (1 mole) of 3,3-bisfluoromethylbutan-2-one in 700 ml of methylene chloride at room temperature such that discolouration was continuous. The solvent was then distilled off under a waterpump vacuum. An almost quantitative yield of 3,3-bisfluoromethyl-1-bromobutan-2-one was obtained as an oil, which could be further reacted directly.

3rd stage

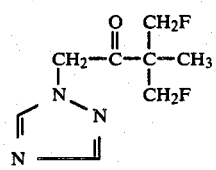

215 g (1 mole) of crude 3,3-bisfluoromethyl-1-bromobutan-2-one were added dropwise to 84 g (1.2 moles) of 1,2,4-triazole and 165 g (1.2 moles) of ground potassium carbonate in 1 liter of ethanol at 30° to 35° C. The mixture was subsequently stirred at 40° C. overnight, the insoluble material was then filtered off and the filtrate was concentrated. The oily residue was extracted with methylene chloride and water and the extract was dried over sodium sulphate and concentrated. The residue was taken up in methylene chloride and 140 ml of ethereal hydrochloric acid were added. The crystalline product formed was filtered off with suction and extracted by stirring with 1 liter of methylene chloride and 1 liter of saturated aqueous sodium bicarbonate solution, and the extract was washed with 1 liter of water, dried over sodium sulphate and concentrated. 73.8 g (36.4% of theory) of 3,3-bisfluoromethyl-1-(1,2,4- triazol-1-yl)-butan-2-one were obtained as an oil, which could be further reacted directly.

4th stage

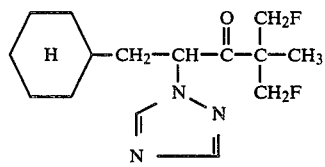
(IV-I)

A solution of 101.4 g (1.81 moles) of potassium hydroxide in 217.2 ml of water was added to a solution of 369.4 g (1.81 moles) of 2,2-bis-fluoromethyl-4-(1,2,4-triazol-1-yl)-butan-3-one in 2 liters of dimethyl sulfoxide at room temperature, with stirring. 320.5 g (1.81 moles) of cyclohexylmethyl bromide were added dropwise to this mixture, with stirring, the temperature of the reaction mixture being kept between 20° and 40° C. by cooling. The reaction mixture was stirred at 60° C. for a further 15 hours and then poured into 2 liters of water. The resulting mixture was extracted twice with 1 liter of methylene chloride each time, the combined organic phases were washed four times with 2 liters of water each time and dried over sodium sulphate and the solvent was stripped off. The oily product which remained was taken up in acetone and 326 g of naphthalene-1,5-disulphonic acid were added to the solution. The precipitate which thereby formed was filtered off with suction and suspended in 2 liters of methylene chloride. This suspension was shaken twice with 2 liters of saturated aqueous sodium bicarbonate solution each time. The organic phase was then washed with 2 liters of water and, after drying over sodium sulphate, was concentrated under reduced pressure. 297.5 g (63% of theory) of 2,2-bis-fluoromethyl-5-cyclohexyl-4-(1,2,4-triazol-1-yl)-pentan-3-one were obtained in this manner in the form of an oil.

$n_D^{20} = 1.4837$.

It will be understood that the specification and examples are illustrative, but not limitative of the present invention and that other embodiments within the spirit and scope of the invention will suggest themselves to those skilled in the art.

What is claimed is:

1. A substituted acetylene-ketone of the formula

in which
$R^1$ is

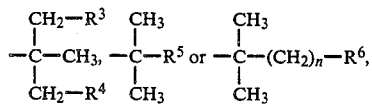

$R^2$ is straight chain or branched alkyl with 1 to 12 carbon atoms, cycloalkenyl with 5 to 7 carbon atoms the cycloalkenyl ring being mono-, di- or tri-substituted by identical or different alkyl radicals with 1 to 4 carbon atoms, or $R^2$ is cycloalkylalkyl with 3 to 7 carbon atoms in the cycloalkyl part and 1 to 4 carbon atoms in the alkyl part, or is cycloalkylalkyl with 3 to 7 carbon atoms in the cycloalkyl part and 1 to 4 carbon atoms in the alkyl part, the cycloalkyl part being mono-, di- or tri-substituted by identical or different alkyl radicals with 1 to 4 carbon atoms, or $R^2$ is phenyl or phenylalkyl with 1 to 4 carbon atoms in the alkyl part, or is phenyl which is mono-, di- or tri-substituted by identical or different substituents selected from halogen, alkyl with 1 to 4 carbon atoms, alkoxy with 1 to 4 carbon atoms, alkylthio with 1 to 4 carbon atoms, halogenoalkyl with 1 to 4 carbon atoms and 1 to 5 identical or different halogen atoms, halogenoalkoxy with 1 to 4 carbon atoms and 1 to 5 identical or different halogen atoms, halogenoalkylthio with 1 to 4 carbon atoms and 1 to 5 identical or different halogen atoms, nitro, cyano, alkoxycarbonyl with 1 to 4 carbon atoms in the alkoxy part, phenyl, halo-substituted phenyl, phenoxy and halo-substituted phenoxy, or is phenylalkyl with 1 to 4 carbon atoms in the alkyl part, which phenyl moiety is mono-, di- or tri-substituted by identical or different substituents selected from halogen, alkyl with 1 to 4 carbon atoms, alkoxy with 1 to 4 carbon atoms, alkylthio with 1 to 4 carbon atoms, halogenoalkyl with 1 to 4 carbon atoms and 1 to 5 identical or different halogen atoms, halogenoalkoxy with 1 to 4 carbon atoms and 1 to 5 identical or different halogen atoms, halogenoalkylthio with 1 to 4 carbon atoms and 1 to 5 identical or different halogen atoms, nitro, cyano, alkoxycarbonyl with 1 to 4 carbon atoms in the alkoxy part, phenyl, halo-substituted phenyl, phenoxy and halo-substituted phenoxy, $R^3$ is fluorine, chlorine or bromine, $R^4$ is hydrogen, fluorine, chlorine or bromine, $R^5$ is straight-chain or branched alkyl with 2 to 6 carbon atoms, straight-chain or branched alkenyl with 2 to 4 carbon atoms, straight-chain or branched alkinyl with 3 to 5 carbon atoms or a group selected from formyl, oxime, oxime ether, acetal, dioxolane, substituted dioxolane, dioxane and substituted dioxane, or $R^5$ is methyl, if $R^2$ is optionally substituted cycloalkenyl or optionally substituted cycloalkylalkyl, $R^6$ is cyano, phenyl, or phenyl which is mono-, di- or tri-substituted by identical or different substituents selected from halogen, alkyl with 1 to 4 carbon atoms, alkoxy with 1 to 4 carbon atoms, alkylthio with 1 to 4 carbon atoms, halogenoalkyl with 1 to 4 carbon atoms and 1 to 5 identical or different halogen atoms, halogenoalkoxy with 1 to 4 carbon atoms and 1 to 5 identical or different halogen atoms, halogenoalkylthio with 1 to 4 carbon atoms and 1 to 5 identical or different halogen atoms, nitro, cyano, alkoxycarbonyl with 1 to 4 carbon atoms in the alkoxy part, phenyl, halo-substituted phenyl, phenoxy and halo-substituted phenoxy, or $R^6$ is the grouping $-XR^7$, wherein $R^7$ is straight-chain or branched alkyl with 1 to 6 carbon atoms, halogenoalkyl with 1 to 4 carbon atoms and 1 to 5 identical or different halogen atoms, phenyl, phenylalkyl with 1 or 2 carbon atoms in the alkyl part, or phenyl which is mono-, di- or tri-substituted by identical or different substituents selected from halogen, alkyl with 1 to 4 carbon atoms, alkoxy with 1 to 4 carbon atoms, alkylthio with 1 to 4 carbon atoms, halogenoalkyl with 1 to 4 carbon atoms and 1 to 5 identical or different halogen atoms, halogenoalkoxy with 1 to 4 carbon atoms and 1 to 5 identical or different halogen atoms, halogenoalkylthio with 1 to 4 carbon atoms and 1 to 5 identical or different halogen atoms, nitro, cyano, alkoxycarbonyl with 1 to 4 carbon atoms in the alkoxy part, phenyl, halo-substituted phenyl, phenoxy and halo-substituted phenoxy, or $R^7$ is phenylalkyl with 1 or 2 carbon atoms in the alkyl part, the phenyl part being mono-, di- or tri-substituted by identical or different substituents selected from halogen, alkyl with 1 to 4 carbon atoms, alkoxy with 1 to 4 carbon atoms, alkylthio with 1 to 4 carbon atoms, halogenoalkyl with 1 to 4 carbon atoms and 1 to 5 identical or different halogen atoms, halogenoalkoxy with 1 to 4 carbon atoms and 1 to 5 identical or different halogen atoms, halogenoalkylthio with 1 to 4 carbon atoms and 1 to 5 identical or different halogen atoms, nitro, cyano, alkoxycarbonyl with 1 to 4 carbon atoms in the alkoxy part, phenyl, halo-substituted phenyl, phenoxy and halo-substituted phenoxy, X is O, S, SO or $SO_2$ and the index n is 0 or 1.

2. A compound as claimed in claim 1, wherein $R^1$ is the grouping —$C(CH_2R^3)$ $(CH_2R^4)CH_3$, in which $R^3$ is fluorine or chlorine and $R^4$ is hydrogen, fluorine or chlorine 3. A compound as claimed in claim 1, characterized by the formula

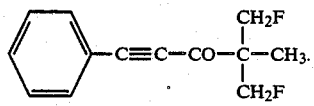

4. A compound as claimed in claim 1, characterized by the formula

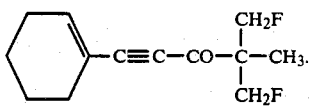

5. A compound as claimed in claim 1, characterized by the formula

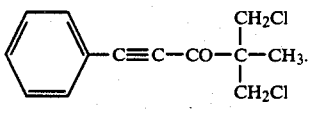

6. A compound as claimed in claim 1, characterized by the formula

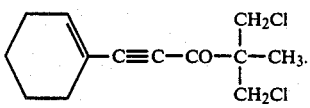

7. A compound as claimed in claim 1, characterized by the formula

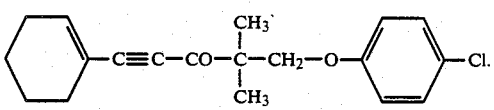

8. A compound as claimed in claim 1, characterized by the formula

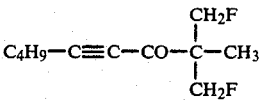

* * * * *